(12) United States Patent
Prescott

(10) Patent No.: US 6,355,426 B2
(45) Date of Patent: *Mar. 12, 2002

(54) METHODS FOR THE CHARACTERIZATION AND SELECTION OF RNA TARGET MOTIFS THAT BIND COMPOUNDS OF PHARMACEUTICAL USE

(75) Inventor: Catherine Denise Prescott, Cambridge (GB)

(73) Assignee: Smithkline Beecham Corporation, Philadelphia, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/297,479
(22) PCT Filed: Oct. 27, 1997
(86) PCT No.: PCT/US97/19239
  § 371 Date: Apr. 30, 1999
  § 102(e) Date: Apr. 30, 1999
(87) PCT Pub. No.: WO98/18947
  PCT Pub. Date: May 7, 1998

Related U.S. Application Data
(60) Provisional application No. 60/029,802, filed on Oct. 31, 1996.

(51) Int. Cl.[7] .......................... C12Q 1/68; C12N 13/00; C12N 15/01; C12N 15/74; C07H 21/04; A01N 34/18; A61K 49/00
(52) U.S. Cl. .................. 435/6; 435/173.1; 435/454; 435/488; 435/489; 435/173.6; 435/320.1; 536/23.1; 536/24.2; 536/253; 514/2; 424/9.1
(58) Field of Search .................. 435/326.1, 6, 173.1, 435/454, 173.6, 488, 489; 536/23.1, 24.2, 25.3; 514/2; 424/9.1

(56) References Cited

U.S. PATENT DOCUMENTS

| 5,270,163 A | * 12/1993 | Gold et al. ..................... 435/6 |
| 5,525,495 A | 6/1996 | Keene et al. ............. 435/172.3 |

(List continued on next page.)

OTHER PUBLICATIONS

Howard et al. Fragmentation of the ribosome to investigate RNA–ligand interactions. Biochem. Cell Biology 73: 1161–1166, Apr. 1996.*

(List continued on next page.)

Primary Examiner—Stephanie W. Zitomer
Assistant Examiner—Cynthia B. Wilder
(74) Attorney, Agent, or Firm—Jason C. Fedon; Edward R. Gimmi; Charles M. Kinzig

(57) ABSTRACT

Methods are disclosed for identifying an RNA fragment that mimics the structure of a defined or undefined target RNA molecule to which a compound binds inside of a cell resulting in retardation of cell growth or cell death. Methods using these RNA fragments for identifying unknown compounds of pharmaceutical interest, and for identifying unknown RNA targets for use in treating disease are disclosed. These methods and compositions are used in screening for novel antibiotics, bacteriostatics, or modifications thereof or for identifying compounds useful to alter expression levels of proteins encoded by mRNA. The methods involve providing random DNA fragments from DNA which encodes RNA target molecules, cloning such fragments to create a plasmid library of same; transfecting cells which contain the native RNA target molecule with the plasmid library and exposing the cells to one or more of test compounds. Cells transfected with an RNA fragment that mimics the target molecule will survive in culture, and cells transfected with fragments which do not mimic the molecule will suffer defects in growth. The mimicking RNA fragment is isolated and provides structural information about the target. The fragment and the information derived from it are then used to screen or design binding compounds.

21 Claims, 5 Drawing Sheets

U.S. PATENT DOCUMENTS

| | | | | |
|---|---|---|---|---|
| 5,593,835 A | * | 1/1997 | Rando et al. | 435/6 |
| 5,610,015 A | | 3/1997 | Wickens et al. | 435/6 |
| 5,677,131 A | | 10/1997 | Wickens et al. | 435/6 |
| 5,834,184 A | * | 11/1998 | Harada et al. | 435/6 |

OTHER PUBLICATIONS

Watson et al. Second Edition, Scientific American books, pp. 214, 223 and 224, Dec. 1993.*

Watson et al. Second Edition, Scientific American Books ISBN 0–7167–2282–8, Dec. 1993.*

Prescott, et al., "A single mutation in 16S rRNA that affects mRNA binding and translation–termination,"*Nucleic Acids Research*, 18: 5381–5386 (1990).

Prescott, et al., "A rRNA–mRNA base pairing model for UGS–dpendent termination," *Biochimie*, 73(7–8): 1121–1129 (1991).

Lloyd, et al., "Inducible Expression of a Gene Specific to the RecF Pathway for Recombination in *Escherichia coli* K12," *Mol. Gen. Genet.*, 190: 162–167 (1983).

Howard, et al., "Fragmentation of the ribosome to investigate RNA–ligand interactions," *Biochem. Cell Biol.*, 73: 1161–1166 (1995).

Prescott, et al., "Mutations in E. coli 16S rRNA that enhance and decrease the activity of a suppressor tRNA," *Nucleic Acids Research*, 20(7): 1567–1571 (1992).

Prescott, et al., "Ribosomes containing the C1054–deletion mutation in E. coli 16S rRNA act as suppressors at all three nonsense codons," *Nucleic Acids Research*, 19(19): 5281–5283 (1991).

Prescott, et al., "A single base change at 726 in 16S rRNA radically alters the pattern of proteins synthesized in vivo," *The EMBO Journal*, 9(1): 289–294 (1990).

Afshar, et al., "Structure–based and combinatorial search for new RNA–binding drugs," *Current Opinion in Biotechnology*, 10: 59–63 (1999).

Thom, et al., "The Selection In Vivo and Characterization of an RNA Recognition Motif for Spectinomycin," *Bioorganic & Medicinal Chemistry*, 5(6): 1081–1086 (1997).

Gontarek, et al., "The N Terminus of Eukaryotic Translation Elongation Factor 3 Interacts with 18 S rRNA and 80 S Ribosomes," *The Journal of Biological Chemistry*, 273(17): 10249–10252 (1998).

Spahn, et al., "Throwing a spanner in the works: antibiotics and the translation apparatus," *Journal of Moledular Medicine*, 74:423–439 (1996).

Pearson, et al., "RNA as a drug target," *Chemistry & Biology*, 4: 409–414 (1997).

* cited by examiner

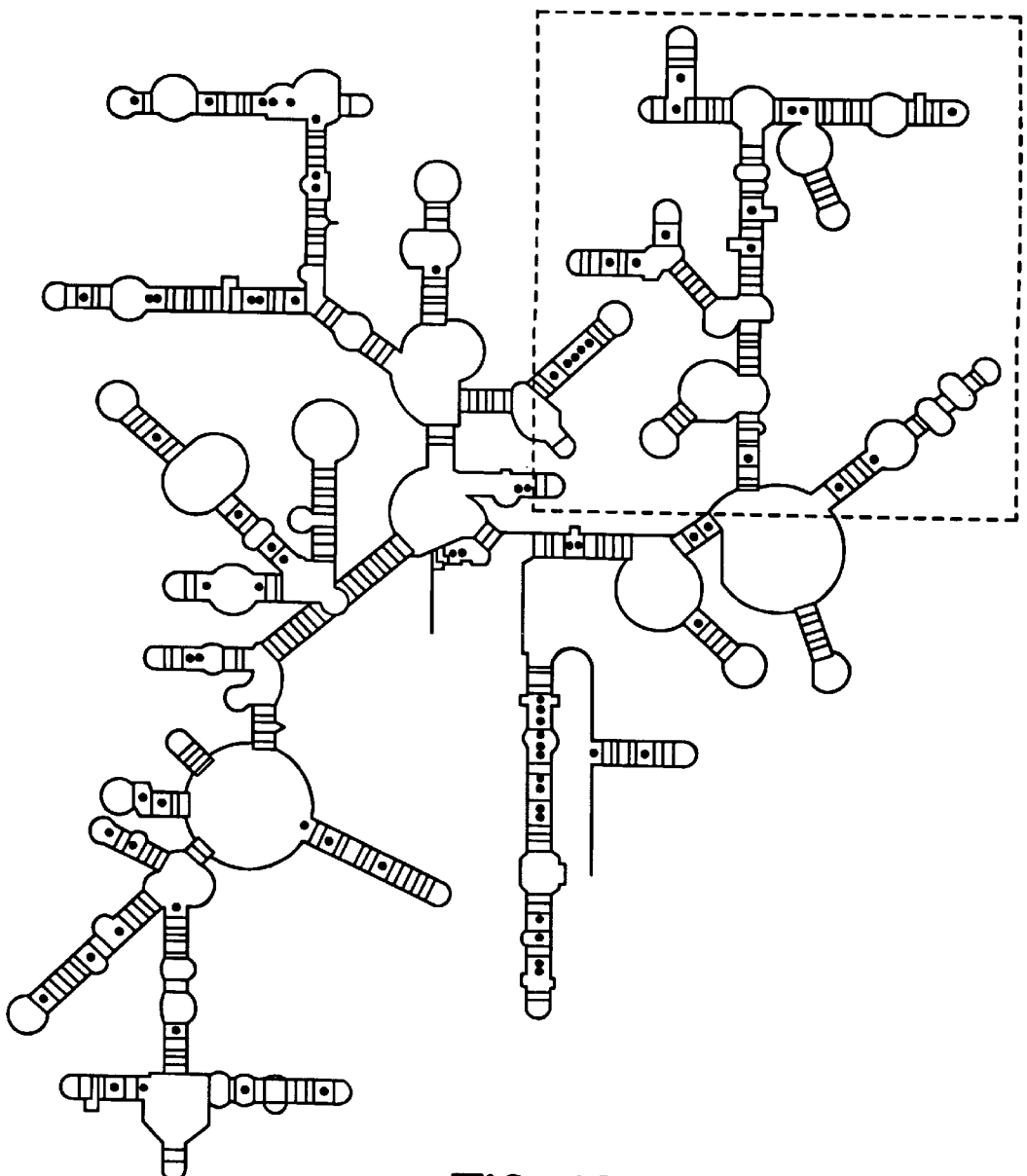
FIG. IA

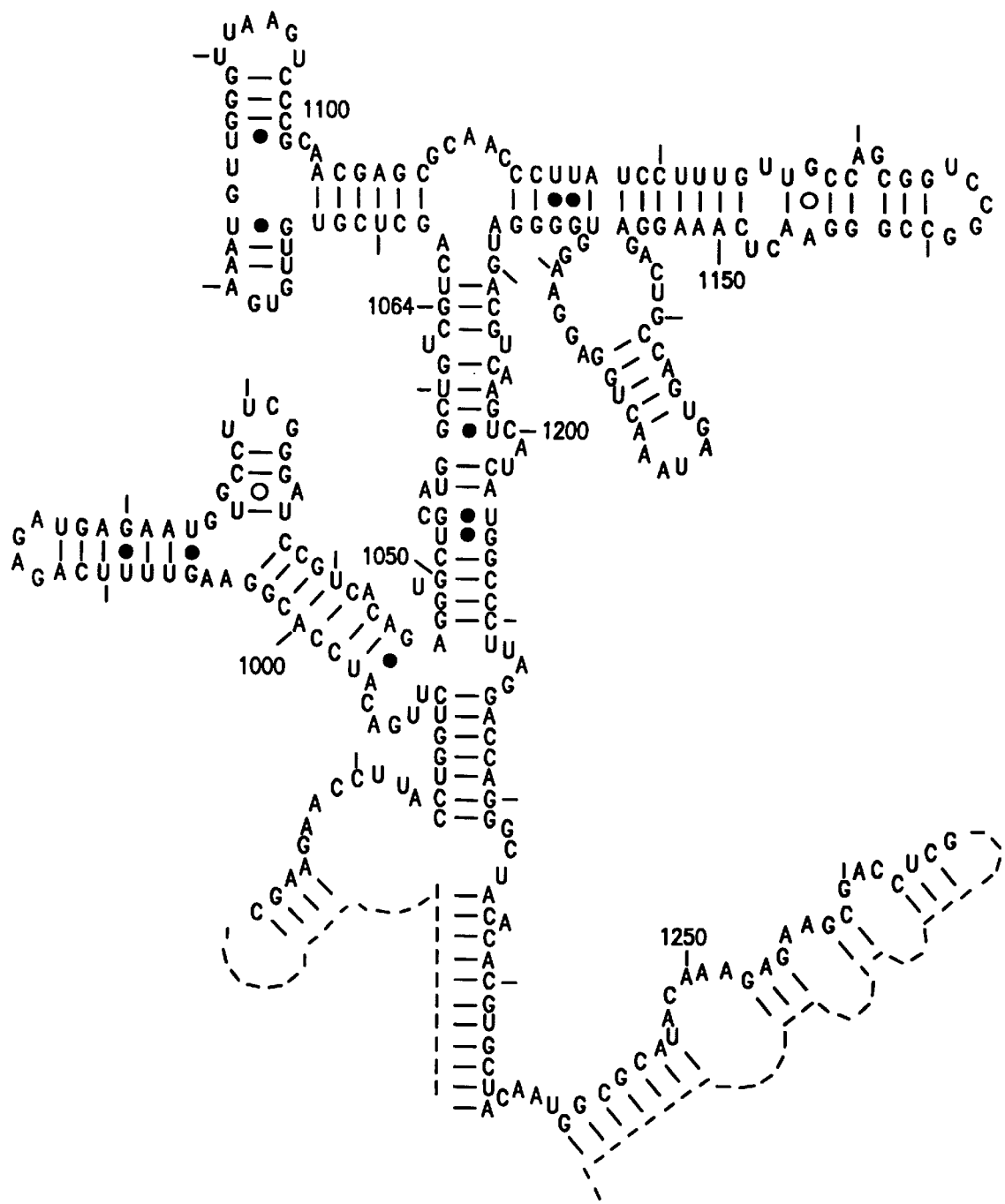
FIG. IB

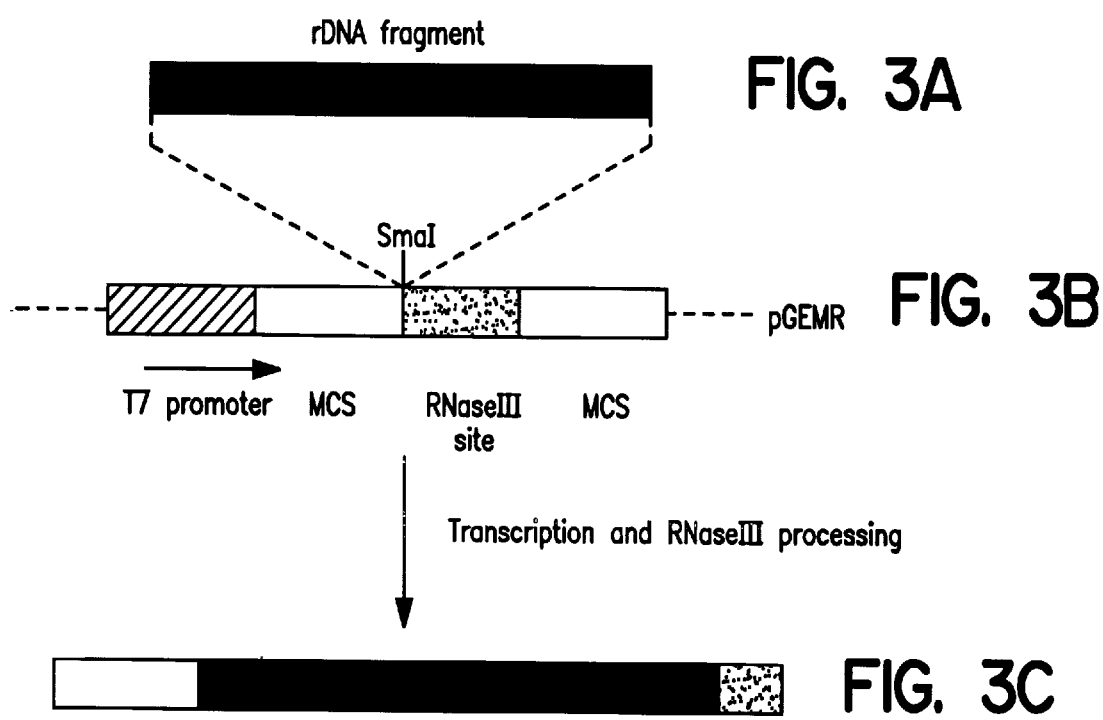

METHODS FOR THE CHARACTERIZATION AND SELECTION OF RNA TARGET MOTIFS THAT BIND COMPOUNDS OF PHARMACEUTICAL USE

This application claims benefit of provisional application 60/029,802 filed Oct. 31, 1996.

FIELD OF THE INVENTION

The present invention relates to the field of pharmaceutical screening methods for novel drugs and for the ribonucleotide targets to which they bind.

BACKGROUND OF THE INVENTION

A ribonucleoprotein (RNP) complex is formed between ribonucleic acid (RNA) and protein. Such RNPs are shown to participate in almost all macromolecular processes, including RNA processing, protein synthesis RNA editing, and the signal recognition of proteins targeted for export. Knowledge of the functional importance of RNA is ever increasing, as exemplified by the indication that, for example, 23S rRNA plays a key role in peptidyl transferase [H. Noller et al., Science, 256:1416–1419 (1992)]. The translation apparatus (i.e., that which decodes RNA for protein synthesis) is essential to all living cells and represents one of the major targets for antibiotics and other pharmaceutically useful compositions.

An understanding of the precise mechanism of drug action is dependent on detailed knowledge at the molecular level, of the structure and function of the drug-RNP complex, e.g., the ribosome and its associating factors. However, such understanding at the molecular level of RNA structure and RNA-ligand interactions has been hampered by the size and complexity of, for example, the ribosome and other RNP particles.

As one example of RNP particles, the ribosome is likely to have evolved from autonomously assembled structural sub-domains. Domain organization occurs within the ribosome. Partial ribonuclease digestion of the 30S subunit releases a RNP complex containing ribosomal proteins (r-proteins) S7, S9, S19, S13, or S14 and fragments derived from the 3' half of 16S rRNA [J. Morgan et al., Eur. J. Biochem., 29:542–552 (1972); A. Yuki et al, Eur. J. Biochem., 56:23–34 (1975)]. Specific RNP particles encompassing the 5' and central domains have also been isolated [R. A. Zimmerman, Ribosomes, (Nomura, M. et al. eds.) Cold Spring Harbor Laboratory, Cold Spring Harbor, N.Y., (1974), p. 225–269]. The small subunit ribosomal RNA (rRNA) from *E. coli* (16S rRNA) is organized into three major domains: the 5', central and 3' domains. Ribosomal RNA fragments representing each of these subdomains can reassemble with specific subsets of ribosomal proteins [Noller, H. F. et al, Science, 212: 402–411 (1981)].

Several lines of evidence support the notion that the ribosome can be fragmented into smaller, functional subdomains that retain organizational and ligand-binding properties characteristic of the intact particle. For example, in vitro assembly of intact 30S subunits have further demonstrated two to three independent nucleation events for various domains within the 30S subunit. This provides a further indication for the existence of independent assembly domains [Nomura, M. et al, J. Cell Physiol., 74: 241–252 (1974); W. A. Held et al., J. Biol Chem., 249:3103–3111 (1974)].

More recently, a fragment corresponding to the 5' domain (nucleotides 1–526) assembled with r-proteins S4, S16, S17, and S20 [C. J. Weitzmann et al., FASEB J., 7:177 (1993)], and a fragment of the 3' domain of 16S rRNA (nucleotides 923–1542) reconstituted together with eight r-proteins formed a structure that resembled the head of the 30S subunit [Samaha, R. R. et al, Proc. Natl. Acad. Sci., 91:7884–7888 (1994)]. This particle retains the property of being able to bind the antibiotic, spectinomycin, which specifically protects the N-7 position of G1064 from attack by dimethylsulphate in both 30S subunits and the sub-particle [Samaha et al, cited above; Moazed, D. et al, Nature (London), 327: 389–394 (1987)].

The degree of protection to both particles shows the same dependence on drug concentration, indicating that spectinomycin binds with similar affinity to each particle. Resistance mutations have been mapped to structural changes in either ribosomal protein S5 or within helix 34 of 16S rRNA formed by base pairing between nucleotides 1046–1065 and 1191–1211 [Brink, M. F. et al, Nucleic Acids Res., 22:325–331 (1994) and Johanson, U. et al, Nucleic Acids Res., 23:464–466 (1995)]. See FIG. 1.

Further dissection of the ribosome has been achieved and expanded to include interactions with ligands other than ribosomal proteins. An oligoribonucleotide analogue of the decoding region located near to the 3' end of 16S rRNA interacts with both antibiotic (neomycin) and RNA ligands (tRNA and mRNA) of the 30S subunit in a manner that resembles normal subunit function {Purohit, P. et al, Nature (London), 370: 659–662 (1994)}. Accordingly, fragmentation of RNP complexes and indeed large RNAs can be considered as a potent strategy in the analysis of such molecules [Schroeder, R., Nature (London), 370:597–598 (1994)].

The binding of the antibiotic, spectinomycin, is independent of S5 indicating that the rRNA is the major determinant of the binding site [Samaha et al, cited above]. The G1064-C1192 base pair is likely directly involved in the binding of spectinomycin as revealed by the chemical footprinting data and the existence of resistance mutations that reflect either a disruption of the base pair or replacement of the base pair [Brink et al, cited above].

Mutations in *E. coli* 16S rRNA that confer spectinomycin resistance include C1192U,G,A, G1064U,C,A, G1064U-C1192A, G1064-C1192G, G1064A-C1192U and C1066U. The major effect of spectinomycin in vitro is proposed to inhibit the translocation of peptidyl-tRNAs from the A-site to the P-site by preventing the binding of elongation factor G (EF-G) to the ribosome [Bilgin, N. et al., EMBO J., 9: 735–739 (1990)]. Helix 34 has been proposed to melt during the elongation cycle and spectinomycin exerts its inhibitory effect by stabilizing the helix [Brink et al, cited above]. Helix 34 has the potential to exhibit two structural conformers similar to the phylogenetic model, without disruption of the overall base pairing arrangement [Prescott, C. D. et al., Biochimie 1991, 73, 1121–1129] (See FIG. 2). The conformers reflect the alternate availability of either an "upper" (1199–1201) or "lower"(1202–1204) 5'-UCA-3' triplet.

To date, characterization of the interaction between drug and rRNA has been based on the above-described in vitro approaches, for example, ligand binding to an oligoribonucleotide analogue of the decoding region located near to the 3' end of 16S rRNA. This RNA fragment interacts with both antibiotic (neomycin) and RNA ligands (tRNA and mRNA) of the 30S subunit in a manner that resembles normal subunit function.

Despite the wealth of research in this area, there remains a need in the art for methods and compositions useful for identifying pharmaceutically useful compounds, e.g., antibiotics, which bind cellular RNA targets.

SUMMARY OF THE INVENTION

As one aspect, the present invention provides a method for identifying an RNA fragment that mimics the structure of a binding site of a target RNA molecule (hereafter referred to as a "mimicking RNA fragment"). In this method, the target molecule is a defined, known RNA molecule. The method includes the steps of providing a defined DNA fragment, by either fragmenting DNA encoding the target RNA molecule with one or more restriction enzymes or chemically synthesizing a DNA fragment encoding a portion of the RNA target molecule. The defined fragment is cloned into a plasmid which, under suitable conditions, permits synthesis of the RNA fragment encoded by the DNA fragment. The plasmid is transfected into a host cell which contains the target RNA molecule. Untransfected host cells are cultured in the presence of a compound which inhibits cell growth or kills the cells. The transfected cells are similarly cultured in the presence of the compound. If the transfected cells permit the synthesis of an RNA fragment that mimics the target molecule, the RNA fragment imparts drug resistance to the transfected cells, which show no appreciable defect in growth. Thereafter, plasmid containing the DNA fragment, which encodes the mimicking RNA fragment, is isolated from the host cell and characterized by conventional means. This defined DNA fragment thus provides a defined mimicking RNA fragment.

In another aspect, the invention provides a method for screening for compounds which bind a mimicking RNA fragment as described above. The method involves providing as a control a untransfected host cell and providing a host cell transfected with a plasmid comprising a DNA sequence encoding the mimicking RNA fragment. Both cells are exposed to a library of compounds. One or more compounds is identified which, inhibits the growth of, or kills, the untransfected cells. One or more of those compounds is identified which has no effect on the transfected cells. The compound meeting both requirements is identified as binding to the defined RNA fragment contained in the transfected cells.

In yet a further aspect, the invention provides another method for identifying an RNA fragment that mimics the structure of a binding site of a defined target RNA molecule, but uses random, not defined, DNA. In this method, the random DNA fragments are provided from the DNA which encodes the defined target. This is done by randomly fragmenting the DNA encoding the target with one or more restriction enzymes to produce multiple and random DNA fragments or by chemically synthesizing random fragments. As described above, a plasmid library is prepared by cloning each fragment into an identical plasmid. The library thus contains plasmids which under suitable conditions permit synthesis of the RNA fragments encoded by the DNA fragments. Following transfection of host cells with the plasmid library, the transfected cells are cultured in the presence of a compound capable of inhibiting growth of, or killing, untransfected host cells. Cells transfected with a plasmid that results in the synthesis of an RNA fragment that mimics the target molecule, are resistant to the compound. Plasmids from the resistant cells are isolated and the DNA encoding the random mimicking RNA fragments are identified and characterized. This method permits identification of a random mimicking RNA fragment from a defined target.

In yet a further aspect of this invention, a method is provided for screening for compounds which bind the random mimicking RNA fragment by providing an untransfected host cell as a control and a host cell transfected with plasmids, each plasmid comprising a random DNA sequence encoding a random mimicking RNA fragment. Both the control and transfected cells are exposed to a library of putative binding compounds. One or more compounds are identified which meet two requirements: (1) inhibit the growth of, or destroy, the controls; and (2) permit normal cell growth in some transfected cells, thereby identifying the compound as binding to a mimicking RNA fragment. A plasmid which contains a random DNA encoding a mimicking RNA fragment is isolated from the unaffected transfected cells, and the random DNA encoding the mimicking RNA fragment is identified and characterized. This method produces a defined DNA fragment encoding a defined RNA fragment for further screening, as provided by the first method described above.

In still another aspect, the invention provides a method for identifying a mimicking RNA fragment of an undefined target RNA molecule as well as a compound that binds the RNA fragment. The method comprising the steps of:

(a) providing random DNA fragments by either randomly fragmenting DNA from a selected source with one or more restriction enzymes to produce multiple DNA fragments or by chemically synthesizing random DNA fragments;

(b) cloning each fragment into an identical plasmid resulting in a library of plasmids which under suitable conditions permits synthesis of the RNA fragments encoded by the DNA fragments, thereby generating a random RNA fragment library;

(c) transfecting the plasmid library into a host cell which contains the RNA target;

(d) culturing the transfected cells in the presence of a library of compounds;

(e) identifying cells which exhibit growth inhibition or cessation in the presence of at least one compound;

(f) identifying cells which are resistant to the deleterious growth effects in the presence of the same compound, which indicates that an RNA fragment expressed by the transfected cell confers resistance to the compound on the cell;

(e) identifying the compound;

(f) isolating plasmids from the resistant cells; and (g) identifying and characterizing from the plasmids of step (f) the DNA encoding a mimicking RNA fragment of the undefined target.

According to one embodiment of the latter method, the method further includes comparing the secondary structure of two or more RNA fragments identified in step (g) which confer resistance to the same compound. A DNA fragment which encodes a common RNA structural motif in the two or more RNA fragments is identified by resort to RNA bioinformatics computer algorithms known in the art. This method thereby aids the identification of a defined RNA fragment of the undefined target molecule.

According to still another embodiment of the latter method, another step involves screening a library of RNA sequences with the defined RNA fragment to determine the source of the defined RNA fragment and identifying the RNA target molecule thereby.

In yet another aspect, the invention provides as a composition an RNA fragment which mimics a binding site of an intracellular RNA molecule, e.g., an RNA fragment which mimics a binding site for spectinomycin. These RNA fragments are identified by the methods described above.

In still a further aspect, the invention provides a DNA sequence which encodes the mimicking RNA fragments.

In yet a further aspect, the invention provides pharmaceutically useful compounds and compositions, which may be antibiotics, bacteriostatics, or compositions which interact with mRNA to alter expression levels of proteins, identified by the methods described above.

Other aspects and advantages of the present invention are described further in the following detailed description of the preferred embodiments thereof.

BRIEF DESCRIPTION OF THE DRAWINGS

FIG. 1A is a schematic drawing of *E. coli* 16S rRNA secondary structure together with the RNA fragment encoded by the BstUI rDNA fragment (in box) encompassing the spectinomycin-binding domain in helix 34 (nucleotides 1046–1065 and 1191–1211).

FIG. 1B is the secondary structure and nucleic acid sequence of the RNA fragment encoded by the BstUI rDNA fragment encompassing the spectinomycin-binding domain in helix 34 (nucleotides 1046–1065 and 1191–1211). Expression of the rRNA fragment (nucleotides 972–1266) encompassing helix 34 (nucleotides 1046–1065 and 1191–1211) confers resistance in vivo to spectinomycin.

FIG. 3A is a schematic representation of an rDNA fragment from an rDNA library.

FIG. 3B is a schematic representation showing the location of the introduction of an rDNA fragment into pGEMR, and illustrates the T7 promoter region, multi-cloning sites (MCS), and RNaseIII site of pGEMR.

FIG. 3C is a schematic representation of the transcript encoded by the recombinant pGEMR based plasmid containing the rDNA fragment (darkest shaded bar).

DETAILED DESCRIPTION OF THE INVENTION

Figure 2A:
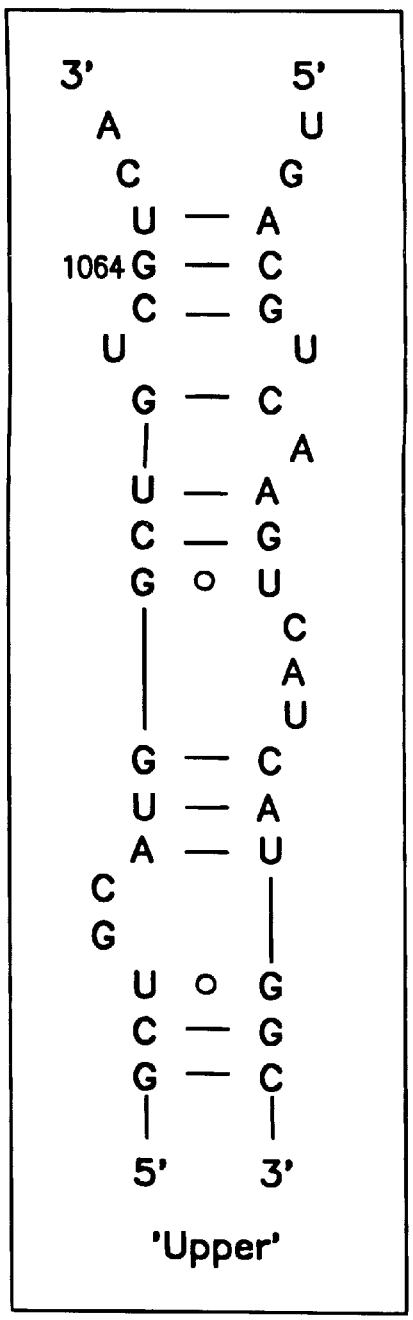
FIG. 2A illustrates the proposed secondary structure conformer of wild-type helix 34, reflecting availability of the 'upper' 5'-UCA-3' triplet.

The present invention provides, among other things, novel "whole cell" methods to dissect large RNA molecules into smaller domains that interact with ligands in a manner that mimics the intact RNA target molecule. Novel methods to identify mimicking RNA fragments of defined and undefined RNA target molecules, methods to use the RNA fragments to identify unknown RNA targets; methods to use the RNA fragments to screen for compounds which bind to the target and have a biological effect on the function of the RNA target molecule, and methods to design useful pharmaceutical compositions are disclosed by this invention.

For example, RNA molecules that confer resistance to pharmaceutical compounds, such as antibiotics or bacteriostatics, can be identified and isolated by the methods of this invention. These RNA molecules may then be used to screen for novel compounds, or used to design improved compounds, which bind the native RNA target and thus function as new or improved drugs. These RNA fragments may also be used to identify novel target molecule/ligand binding pairs.

I. Definitions

As used herein, the term in vivo means within the microorganism, e.g, the bacterial cell or yeast cell; in addition to meaning within an infected cell, e.g., a mammalian cell infected by a virus.

As used herein, the term "target RNA" or "target RNA molecule" means an oligoribonucleotide sequence or ribonucleic acid sequence, which alone or in a ribonucleoprotein complex, contains a binding site for a compound. When the target RNA molecule is in its native environment, i.e., inside a cell, and the cell is exposed to this compound, the compound binds to the binding site of the target RNA and cell growth is either retarded or the cell is killed.

The term "defined target RNA molecule" means a known RNA molecule or a predetermined RNA target sequence. For example, a defined target RNA molecule is a predetermined RNA sequence from a microorganism, an RNA expressed by a cell infected with a virus, and a predetermined RNA sequence present in a mammalian cell, an RNA sequence encoded by a predetermined genomic sequence; and an RNA sequence encoded by a chemically synthesized DNA sequence.

The term "undefined" or "nondefined" target means an unknown RNA molecule or unknown RNA sequence, including a random RNA sequence.

Generally, for use in this invention, the target RNA is RNA, including ribosomal RNA, RNA encoded by a gene, messenger RNA, UTRs, ribozyme RNA, catalytic RNA, small nuclear RNA, small nucleolar RNA, etc., from a microorganism, or an RNA expressed by a cell infected with a virus, or RNA from a host cell, or RNA encoded by a genomic sequence; or RNA encoded by a chemically synthesized DNA sequence or random RNA encoded by randomly isolated DNA. For example, the target may be a bacterial enzyme, a Hepatitis C virus packaging signal, the mRNA encoding for ribonucleotide reductase, among others.

Also as used herein, the term "mimicking RNA fragment" defines a fragment of the RNA target molecule which is able to assume the conformational structure required to mimic the binding site for the compound and thus is able to bind the compound in the same or similar manner and with the same or similar avidity to the naturally occurring target RNA molecule.

The term "microorganism" means bacteria, yeast, fungi, protozoa, parasites or virus or other microorganisms. Preferably the microorganism is a pathogenic microorganism. However, this is not essential. Organisms of the same species as a pathogenic microorganism can share the same or similar RNA target molecules and thus, the same or homologous species microorganism can be used in the methods of this invention. Desirable microorganisms are *S. aureus, S. pneumoniae,* and viruses such as HIV and HCV, among many others. The identity and type of microorganism is not a limitation of this invention.

The term "defined DNA fragment" is a DNA fragment of predetermined sequence.

The term "host cell" as used herein means a cellular microorganism, e.g., a bacterium; or a normal mammalian cell; or a mammalian cell infected with a selected virus, which expresses an RNA molecule due to this infection. The host cell may naturally contain the RNA target molecule, i.e., the intact ribosome, or other RNP. Alternatively, the host cell may have been previously transfected to contain the random RNA target selected by the art. Host cells are genetically engineered (transduced or transformed or transfected) with the plasmids of this invention. The host cell useful in the methods may be the same species as the cellular source of the DNA sequences which encode the RNA target molecule. For example, where the DNA encoding the target was obtained from S. aureus, the host cell useful in the method may be S. aureus. The host cell may alternatively be a related species to the species which provided the DNA. The related species must have the same or similar RNA target. For example, where the DNA encoding the target was obtained from S. aureus, the host cell useful in the method may be E. coli. As shown in the examples below, both species are susceptible to the antibiotic spectinomycin. In still another alternative, where the target RNA molecule source is a virus, the host cell is a species susceptible to infection by that virus, i.e., a mammalian cell. For example, where the RNA target is RNA expressed by a vitally infected monkey cell, the host cell may be another infected monkey cell. Where the RNA target is a molecule occurring naturally in a mammalian cell, and the intent is to find a compound to alter expression of that molecule, the host cell may be an uninfected cell of another related mammal having the same or similar RNA target molecule.

The term "compound" as used herein may refer to pharmaceutically useful compounds which kill the cell which naturally contains the target, e.g., antibiotics, bacteriocides. Such compounds may be those which retard the growth of undesirable sources of the target, e.g., bacteriostatic or yeast inhibitors. Still other compounds of pharmaceutical interest include compounds which bind the target and result in another desired effect, such as by altering or inhibiting the function or expression of the product of the RNA target molecule, where such function is deleterious to the host, e.g., such as antibiotic compounds, anti-fungal compounds, bacteriostatic compounds, etc.

II. Identifying a Mimicking RNA Fragment of a Defined RNA Target Molecule

In one embodiment, the method of the invention enables identification of an RNA fragment that mimics the structure of a binding site of a defined target RNA molecule, for example, an RNA enzyme. This method can be performed in two ways: (1) the first in which the DNA encoding the RNA target molecule is defined, i.e., predetermined; or (2) the second, in which the defined DNA sequence encoding the RNA target is randomly fragmented.

According to the first method, the following steps are performed.

First, DNA which encodes the target RNA molecule is extracted from the source of the target, e.g., microorganism, mammalian cells, etc, by conventional means such as described in texts [see, e.g., Sambrook, J. et al., "Molecular Cloning. A Laboratory Manual, 2d edit.; Nolan, C. Ed.; Cold Spring Harbor Laboratory, Cold Spring Harbor, N.Y. (1989). The DNA is provided by digesting it with one or more restriction enzymes to produce one or more defined DNA fragment(s). Alternatively, the defined DNA fragment(s) may be chemically synthesized.

If restriction enzymes are used for this purpose, they may be selected from among the many enzymes known to the art for digesting deoxyribonucleotide sequences. One of skill in the art is expected to know and be capable of selecting appropriate enzymes. The choice of enzymes is not a limitation on the method of this invention.

Second, the DNA fragment(s) are cloned by conventional techniques into a plasmid which under suitable conditions permits synthesis of the RNA fragment encoded by the DNA fragment. Cloning techniques are conventional to the art, as are suitable plasmid constructs. See, e.g., Sambrook, J. et al., cited above]. The selection of appropriate plasmid sequences and components thereof, e.g., promoters, origins of replication, etc., is not a limitation on the methods of this invention. For example, plasmids may be of bacterial, viral, yeast, fungal, insect cell or other origin. The term "plasmid" as used functionally here may be, for example, in the form of a viral particle, a phage, etc, i.e., any construct which is capable of expressing the RNA fragment in the host cell. Preferred plasmids are E. coli pBR322-based plasmids, as well as other plasmids which may be purchased commercially.

Specifically desirable plasmid components are a control sequence, such as a promoter, which directs synthesis of RNA. Common useful promoters are the LacZ promoter, T7 promoter, the Taq promoter and others. Also useful is a transcription termination signal recognized by the host cell polymerases. Other components include signals that permit the RNA processing stem to provide a natural 5' and 3' end on the RNA fragments, e.g., an RNAse III processing signal. Another optional component of the plasmids useful in this invention is a sequence encoding a transcript, desirably encoding a reporter gene, such as beta-galactosidase or green fluorescent protein. When placed in the appropriate proximity to the DNA fragment insert, the plasmid produces a fusion transcript made of the DNA fragment fused to the reporter mRNA. Techniques to design such plasmids are known to the art, and need not be repeated in detail here. An exemplary plasmid is described in Example 1 below.

According to this method, the plasmid library is then transfected into a host cell which contains the intact RNA molecule.

Both untransfected host cells and these transfected host cells are cultured in the presence of one or more test compounds, individually. The culture conditions can include conventional nutrient media modified as appropriate for activating promoters, selecting transformants or amplifying the RNA sequences of the present invention. The culture conditions, such as temperature, pH and the like, are those previously used with the host cell selected for expression, and will be apparent to the ordinarily skilled artisan.

The test compound may be a compound known to bind the binding site of the target RNA molecule inside the host cell, resulting in inhibition of, or cessation of, cell growth. In other methods of this invention, the compound may be a compound which has an unknown activity vis-a-vis the host cell.

One then determines if the cells transfected with the plasmid permit the synthesis of an RNA fragment that mimics the target molecule. This is determined by detecting resistance to the compound's activity in the transfected host cells.

Host cells transfected with DNA fragments which do not mimic the binding site of the intact target molecule to which the drug binds will respond to the compound in the same way as untransfected host cell will. Thus, if the compound retards cell growth, both untransfected cells and cells transfected with DNA fragments which encode RNA fragments which do not mimic the target will evidence retarded or inhibited growth.

However, according to the present invention, cells which have been transfected with an RNA fragment that mimics the target molecule binding site, i.e., a fragment that is capable of folding into a structure which acts to bind the compound in the same or similar manner as the intact RNA molecule, will evidence resistance to the drug/compound.

Without wishing to be bound by theory, the inventors speculate that in such transfected cells, the compound has an increased probability of binding to the naked RNA fragment due to its level of expression relative to its native target, e.g., a RNP complex, likely reflecting for example a higher level of RNA fragment. Thus, the expression (or possibly, the overexpression) of such RNA fragments in the host cell binds the compound, sequestering it within the cell where it has no, or reduced, effect on growth of the cell. This binding or sequestration of the compound by the mimicking RNA fragment decreases the probability that the compound will be available to bind the native RNA target molecule of the host cell. This result permits the continued functioning of the intact RNA molecule and thus normal cell viability. With respect to ribosome targets in particular, the binding of the compound to the mimicking RNA fragment (in the absence of protein) is believed to be due to the fact that the RNA fragments are constitutively expressed in comparison to the expression of the ribosomal proteins and intact rRNAs, which are strictly and coordinately regulated in response to the cellular growth rate. Therefore, the protein is less likely to be available to bind the compound.

Therefore, from such surviving cells, the DNA fragment which encodes the mimicking RNA fragment can be isolated, i.e., from agarose gel or other means standard in the art. The isolated DNA and mimicking RNA fragment may then be sequenced and characterized, also by conventional means in the art.

According to the second method for identifying an RNA fragment that mimics the structure of a binding site of a defined target RNA molecule, in which the DNA encoding the RNA target is an undefined DNA, i.e., random fragments of DNA, the method steps are as follows.

DNA encoding the RNA target molecule obtained from the source as described above is either randomly fragmented with one or more restriction enzymes to produce multiple DNA fragments or chemically synthesized random fragments. As above, each fragment is cloned into a plasmid resulting in a library of plasmids which under suitable conditions permits synthesis of the RNA fragments encoded by said DNA fragments. This generates a random RNA fragment library, which is used to transfect into a host cell which contains said target RNA molecule in a manner similar to that described above.

Transfected host cells are cultured in the presence of a test compound as described for the first method and those cells are identified which are transfected with a plasmid that permits synthesis of an RNA fragment that mimics the target molecule. In other words, transfected cells evidencing resistance to the effect of the drug are selected in contrast to untransfected host cells or on transfected host cells transfected with a plasmid that does not permit synthesis of a mimicking RNA fragment, which cells exhibit growth inhibition or cessation.

Plasmids from resistant cells are isolated; and the DNA encoding the mimicking RNA fragments from those plasmids are characterized as described above. This embodiment of the method thus allows one to define mimicking RNA fragments.

The above-described methods are useful in identifying a mimicking RNA fragment wherein the RNA target molecule is defined. As one example, this method is useful in identifying a mimicking RNA fragment from a microorganism containing an RNA target molecule known to be susceptible to the antibiotic spectinomycin.

III. The Defined RNA Fragment and Its Uses

The RNA fragment which is capable of mimicking the ligand binding site of the defined RNA target molecule, where the ligand/compound is capable of affecting the growth rate of the cell, the infected cell, or the virus, depending on the selection of the RNA target source, can be used to screen for alternative ligands, e.g., alternative novel antibiotic compounds or modified known antibiotic compounds, which can function in the same or similar way as the known antibiotic functions.

Thus, another method of this invention involves screening for compounds which bind a defined RNA fragment that mimics a binding site present on a target RNA molecule. Described briefly, such a method involves exposing a mimicking RNA fragment obtained as described above that mimics a binding site present on the target RNA molecule to a library of compounds; and identifying any compound which binds to said fragment. One means of detecting the binding would be by labeling or immobilizing the compounds or the mimicking fragments. Conventional assay techniques may be employed for such a screening assay. Any compound which binds to the RNA fragment may then be exposed to an untransfected host cell to detect inhibition or cessation of cell growth.

In another embodiment, this method includes the steps of (a) providing an untransfected host cell as a control; (b) providing a host cell transfected with a plasmid containing a DNA sequence encoding the defined mimicking RNA fragment; (c) exposing both transfected and untransfected host cells to a library of compounds; (d) identifying a compound in the presence of which the growth of untransfected cells is inhibited or destroyed; and in the presence of which, normal growth is observed for transfected cells. A compound satisfying these two requirements is identified as binding to the defined RNA fragment.

In another embodiment of this invention, a method is provided for screening for compounds which bind a random mimicking RNA fragment. The steps of this method involve (a) providing an untransfected host cell as a control; (b) providing a host cell transfected with plasmids, each plasmid containing a random DNA sequence encoding a random RNA fragment which mimics the binding site of the target RNA molecule; (c) exposing both transfected and untransfected cells to a library of compounds; (d) identifying a compound in the presence of which the growth of untransfected cells is inhibited or destroyed; identifying for the same compound transfected cells which experience normal growth in the presence of the compound. Such a compound is identified as binding to a mimicking RNA fragment. A plasmid isolated from the normally growing host cells contains a DNA sequence encoding a mimicking RNA fragment. The DNA sequence is isolated and characterized, resulting in a defined DNA fragment encoding a defined RNA fragment for further screening.

Alternatively, for example, the conformational structure of the RNA fragment which mimics the binding site can be employed in rational drug design to modify known antibiotics to make them bind more avidly to the target. One such methodology is nuclear magnetic resonance (NMR), which is useful to identify drug and RNA conformational structures. Still other methods are, for example, the drug design methods as described in International publication No. WO95/353617 published Dec. 28, 1995; or U.S. Pat. No. 5,322,933, the crystal structure of the RNA fragment can be deduced and computer programs utilized to design novel binding compounds which can act as antibiotics.

IV. Identifying a Mimicking RNA Fragment of a Non-Defined RNA Target Molecule The present invention also provides a method for identifying an RNA fragment that mimics the structure of a binding site of an undefined target RNA molecule. In this aspect of the invention, the method permits identification of a compound that binds the RNA fragment. Undefined RNA targets can include a random RNA sequence selected from, for example, RNA encoded from DNA from a microorganism, an RNA expressed by a cell infected with a virus, and an RNA sequence present in a mammalian cell, an RNA sequence encoded by a random genomic sequence; or an RNA sequence encoded by a library of chemically synthesized DNA sequences.

In this embodiment, DNA from the selected source (as described above) is randomly fragmented with at least one restriction enzyme to produce multiple DNA fragments. Alternatively, the DNA is chemically synthesized as random fragments. As before, each fragment is cloned into a plasmid resulting in a library of plasmids which under suitable conditions permits synthesis of the RNA fragments encoded by the DNA fragments, thereby generating a random RNA fragment library. By conventional means, the plasmid library is transfected into a host cell which contains the undefined RNA target. The transfected host cells are cultured in the presence of a library of compounds.

Host cells which exhibit growth inhibition or cessation of growth in the presence of a test compound are identified and the compound identified. These growth characteristics indicate that the test compound has an effect on the host cell of inhibiting or ceasing cell growth. Host cells which are resistant to these growth effects in the presence of the same compound are detected, which indicates that an RNA fragment expressed by the transfected cell confers resistance to the compound on the host cell.

The compound or compounds in the library of compounds which cause both effects on transfected and untransfected cells are identified. Plasmids from the resistant cells are isolated and the DNA fragments encoding RNA fragments which mimic the binding site of the compound on the undefined target are identified and characterized.

V. Uses of the Undefined RNA Fragments of the Undefined Target

The secondary structure of two or more mimicking RNA fragments from the undefined targets, which react similarly to the same test compound or to related test compounds as obtained above are compared. Generally, the secondary structures are determined by resort to chemical and enzymatic probing methods, such as the conventional methods described in C. Ehresmann et al, *Nucl. Acids Res.*, 15:9109–9128 (1987). The data from these analyses can be used to develop computer algorithms for searching a genomic sequence database, such as described by Lisacek et al, *J. Mol. Biol.*, 235:1206–1217 (1994); Dandekar and Sibbald, *Nucl. Acids Res.*, 18:4719–4725 (1990); and Dandekar and Hentze, *TIG*, 11:45–50 (1995).

A DNA fragment which encodes a common RNA structural motif in these two or more RNA fragments is identified, thereby identifying a defined RNA fragment of the target molecule. This defined fragment can then be used in the screening methods described above in Part III.

Further the defined DNA fragment encoding the defined mimicking RNA fragment can now be employed to screen a library of random DNA sequences to determine the source of said RNA target molecule, and/or to identify or define the intact target molecule. For example, the DNA fragment encoding the mimicking RNA fragment of the undefined target may be used as a probe in conventional methodology, such as polymerase chain reaction, or modifications thereof to identify an unknown full-length target of a known compound in genomic DNA. For example, the sequenced fragment may be used as a PCR probe to isolate and express the full length native molecule. It can be used as a probe in conventional techniques, such as Northern or Western blots to identify the target.

More readily, the mimicking RNA fragment may be employed in conventional screening methodology to select novel compounds or modified compounds which function as desired as well as to identify unknown RNA targets.

VI. Other Assay Formats

In still another embodiment, where the RNA target and/or useful compound are unknown, a screen method may employ both combinations of the methods described above. For example, DNA from a selected microorganism or other source is obtained, fragmented and a plasmid library and transfected host cell library created as provided above. Because the RNA target is unknown, as well as the effective compound, the screening technology is more complicated.

Untransfected cells are used as controls. Each transfected host cell is duplicated or split to provide a separate culture for the number of unknown compounds to be tested. Thus, except for the control, duplicates of each transfected cell and duplicates of the untransfected control cells are subjected to a different compound. The effects of different compounds are examined to determine if any compound retards the growth of, or kills, the controls. If certain compounds do not retard the growth of or kill the controls, they may be discarded from the screen. For those compounds which have such an adverse effect on cell growth on the controls, i.e., which function as antibiotics, the effect on the transfected cells are next observed. If for any individual compound that has adversely effected the growth of the control, there are no surviving or normally growing transfected cultures, then none of the fragments are capable of mimicking the binding, or the target is not the cell's RNA, and that compound is identified as a drug, e.g., as a putative antibiotic, without an identifiable target. Such information is useful in the pharmaceutical industry.

The compounds retained by the screen are those which allow at least one transfected cell culture to grow normally and survive, indicating the occurrence of drug resistance. Isolation of that transfected cell and the RNA fragment contained within it provides a putative antibiotic, as well as a binding site mimicking RNA fragment, which can be used as described above.

Thus, the methods and compositions of the present invention permit selection and/or design of novel drugs, modified drugs, and identification of RNA fragments useful in drug design and in identification of their RNA targets.

Each reference disclosed herein is incorporated by reference herein in its entirety.

Any patent application to which this application claims priority is also incorporated by reference herein in its entirety.

VII. Examples

The present invention is exemplified below by demonstrating use of the method for the interactions between the antibiotic, spectinomycin and its RNA target. According to this invention, an RNA molecule or fragment has been isolated which contains sequences in common with the spectinomycin-binding site in the ribosomal 16S subunit, helix 34. The expression of the isolated 16S rRNA fragment (nucleotides 972–1266), encompassing the spectinomycin binding domain in helix 34, and its use in a screening method, demonstrates that this RNA fragment is sufficient to confer resistance to spectinomycin to the cell. The sequences for the 16S rRNA are obtained as described in Stern et al, *J. Mol. Biol.*, 200:291–299 (1988); Stern et al, *J. Mol. Biol.*, 201:683–696 (1988); and Stern et al, *J. Mol. Biol.*, 204:447–481 (1988), and deposited as NCBI Sequence Identification No. 174375 [Carbon et al, *Eur. J. Biochem.*, 100:399–410 (1979)].

Also illustrated below is the selection of transformants encoding additional RNA fragments that confer resistance to spectinomycin from amongst a large and random pool of RNA fragments. The 16S/23S hybrid molecule (FIG. 4) lacks the sequences characteristic of those flanking helix 34 in 16S rRNA, indicative of their not being essential to formation of the spectinomycin binding site.

The following examples demonstrate whole cell approaches using fragmented RNA molecules to provide detailed information about the molecular recognition of RNA-ligand interactions present in ribonucleoprotein particles. These examples illustrate several embodiments of this invention. These examples are illustrative only, and do not limit the scope of the present invention.

EXAMPLE 1

Strains and Plasmids

A. Bacterial Strains

*E. coli* strains used in these experiments were DH5a [Hanahan, D., *J. Mol. Biol.*, 166: 557–580 (1983)], JM109 [Yanisch-Perron et al., *Gene*, 33: 103–119 (1985)]; and DC2 [Clark, *FEMS Microbiol. Lett.*, 21:189–195 (1984)]. DC2 harbors a mutation that affects membrane permeability and therefore exhibits an increased sensitivity to antibiotics.

B. Plasmid pGP1-2

Plasmid pGP1-2 is a pACYC derivative encoding the T7 Polymerase [Tabor, S. et al, *Proc. Natl. Acad. Sci.*, 83: 1074–1078 (1985).

C. Plasmid pGEMR

Plasmid pGEMR was designed to maximize the stability of rRNA fragments expressed in vivo. It is a derivative of pGEM3Z (Promega) in which two synthetic complementary oligomers encoding the RNase III processing signal [Dunn and Studier, *J. Mol. Biol.*, 166: 477–535 (1983)], were directionally cloned into EcoRI and BamHI restriction sites within the multicloning region present on pGEM3Z, which are immediately downstream of the T7 promoter. The RNaseIII cleavage site sequence is characteristic of that present in precursor rRNA transcripts [Bram, R. J. et al, *Cell*, 19: 393–401 (1980)]. The oligomer sequences included a unique SmaI site upstream of the RNase III site (FIG. 3) for the insertion of DNA encoding the RNA fragments. Thus, DNA fragments encoding the RNA molecules of interest can be blunt end ligated in to the SmaI site and expressed from the upstream T7 promoter.

In this construct, the RNA fragment transcripts are predicted to be processed by the nuclease, generating a 'native' 3' terminus equivalent to that on mature rRNAs. In vivo processing at the RNase III site should ensure the expression of transcripts with a defined length.

D. Plasmid pGEMR294

A fragment of 16S rDNA (nucleotides 972–1266) that encompassed helix 34 [Brimacombe et al., *J. Mol. Biol.*, 199:115–136 (1988)] (See, FIG. 1) was cloned and expressed. A series of spectinomycin-resistant mutations have been mapped to this region [Sigmund et al., *Nucl. Acids Res.*, 12:4653–4663 (1984); Makosky et al., *Biochim.*, 69:885–889 (1987); Brink et al., *Nucl. Acids Res.*, 22:325–331 (1994); Johanson and Hughes, *Nucl. Acids Res.*, 23:464–466 (1995)]. The *E. coli* 16S rDNA ApaI-SmaI fragment (nucleotides 932–1384) was isolated and subsequently restricted to release a BstUI fragment derivative (nucleotides 972–1266). This was blunt-end cloned into pGEMR generating pGEMR294.

Plasmids were isolated using the QIAGENTIPÔ systems according to manufacturers recommendations. Sequence analysis was as according to the fMOL Sequencing system (Promega) using forward and reverse primers complementary to the T7 promoter and RNase III cleavage site.

EXAMPLE 2

In Vivo Expression Studies

The first in vivo approaches toward dissecting RNA, ribosome or random library, into functional subdomains are disclosed here. In the first approach (Example 2A), a specific rRNA fragment encompassing helix 34 was cloned and the transformants examined for tolerance to growth in the presence of spectinomycin. The second approach (Example 2B) generated a random library of rRNA fragments and selected for transformants present within the entire library that were resistant to spectinomycin.

As disclosed below, both approaches resulted in the identification of RNA fragments that either encompassed the wild type helix 34 or a molecule that could be predicted to fold at the secondary structure level in a manner that resembles helix 34.

A. A Defined 16S rRNA Fragment Confers Spectinomycin Resistance

Chemical footprinting studies have shown that spectinomycin interacts with G1064 in helix 34 (nucleotides 1046–1065 and 1191–1211) [Moazed et al., *Nature* (London), 334:362–364 (1988)]. As disclosed above, a series of spectinomycin resistant mutations have been constructed within this region [Brink et al., and Johanson and Hughes, both cited above]. The inventors demonstrate by this experiment that in vivo expression of an RNA fragment encompassing helix 34 sequesters spectinomycin and consequently permits the continued functioning of the ribosome and thereby confers drug resistance to the whole cell.

*E. coli* strains DH5a and JM109 were conventionally transformed with pGP1-2, and were subsequently transformed by pGEMR (control) and pGEMR294 (which contains the 16S sequence) as described above in Example 1D. Transformants were selected on LB agar containing ampicillin (200 ug/mL) and kanamycin (50 mg/mL). These transformants were subsequently examined for their ability to grow in the presence of varying concentrations of spectinomycin (5, 10, 15, 20 and 40 ug/mL). Spectinomycin resistant transformants were recovered at 37° C.

Transformants of pGEMR did not survive on plates containing concentrations of spectinomycin above 5 mg/mL. By contrast, transformants of pGEMR294 grew in the presence of the drug up to 20 mg/mL. Plasmids isolated from the transformants and used to retransform each strain, confirmed that resistance was indeed plasmid dependent.

Therefore, the simplest interpretation of the result was that the rRNA fragment encompassing helix 34 was expressed at a sufficient level and formed a structure able to bind spectinomycin, thereby conferring drug resistance.

Therefore, the expression of this 16S rRNA fragment sequestered, and therefore decreased the inhibitory action of, spectinomycin on the cell and is proposed to reflect the correct folding of the RNA molecule to allow spectinomycin binding.

B. In Vivo Selection of RNA Fragments that Confer Spectinomycin Resistance—Expression of Random RNA Fragments This experiment describes in vivo expression of different rRNA fragments plated in the presence of spectinomycin. The potential of the in vivo RNA fragment rescue approach was further investigated by screening for spectinomycin resistant transformants from amongst a population of cells encoding a library of rRNA fragments.

Random rDNA fragments were generated by restriction endonuclease digestion of the entire rrnB operon encoding all three rDNAs (16S, 23S and 5S) and the spacer regions using a range and combination of one or more enzymes (including either AluI, HaeIII or DpnI or a double digestion with AluI/DpnI or HaeIII/DpnI) in which recognition sites occurred frequently within the target sequence. The enzymes AluI, HaeIII and DpnI release fragments that can be cloned in either orientation in to the SmaI site on pGEMR.

The fragments were ligated into the SmaI site in pGEMR and used to transform the respective strains. The diversity of RNA fragments within the library was determined by in vitro transcription of radiolabeled transcripts using the RIBOMAXÔ system (Promega), resolution by denaturing gel electrophoresis, and autoradiography according to standard procedures [Sambrook et al, cited above]. Briefly described, to establish that the pool of transformants harbored pGEMR encoding a mixed population of rRNA fragments, the plasmids were isolated, linearized with HindIII and transcribed in vitro with T7 RNA polymerase in the presence of $^{32P}$aUTP. The products were resolved by denaturing gel electrophoresis and visualized by autoradiography. The library consisted of a large number of transcripts, varying in size with an average of 200–500 nucleotides in length.

E. coli strain DC2 was transformed with pGP1-2 and was subsequently transformed by this mixed library of fragments and plated onto ampicillin (200 mg/mL) and increasing concentrations of spectinomycin (10, 20, 40 and 80 ug/mL) and incubated at 37° C.

Spectinomycin-resistant transformants grew slowly, developing after 48 hours incubation on plates containing up to 40 ug/mL spectinomycin. Their plasmids were isolated and used to retransform DC2 (containing pGP1-2) to confirm that the resistance phenotype was attributable to the plasmid. The cloned fragments were subsequently characterized by sequencing.

Figure 2B:
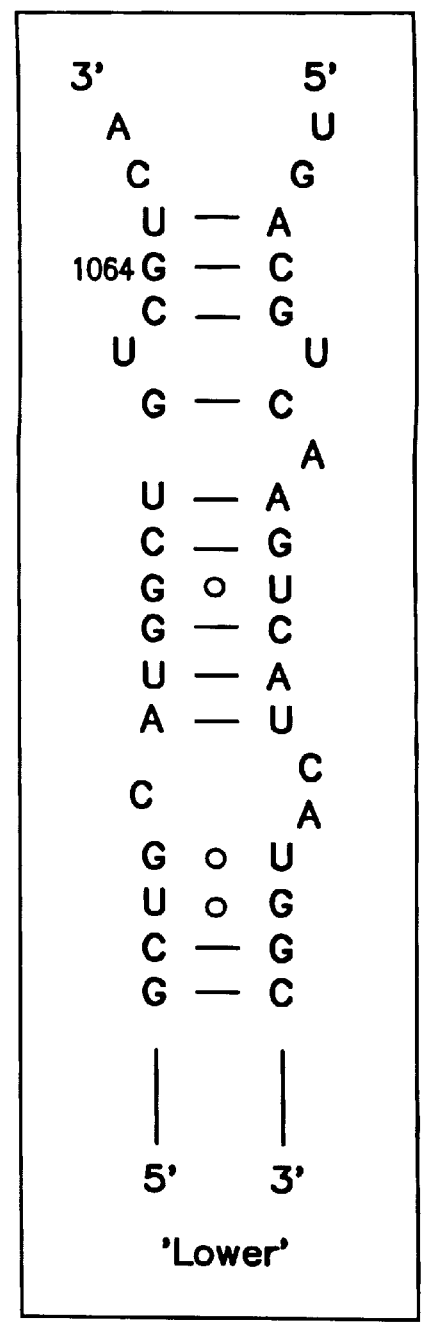
FIG. 2B illustrates the proposed secondary structure conformer of wild-type helix 34, reflecting availability of the 'lower' 5'-UCA-3' triplet.
Figure 4A:
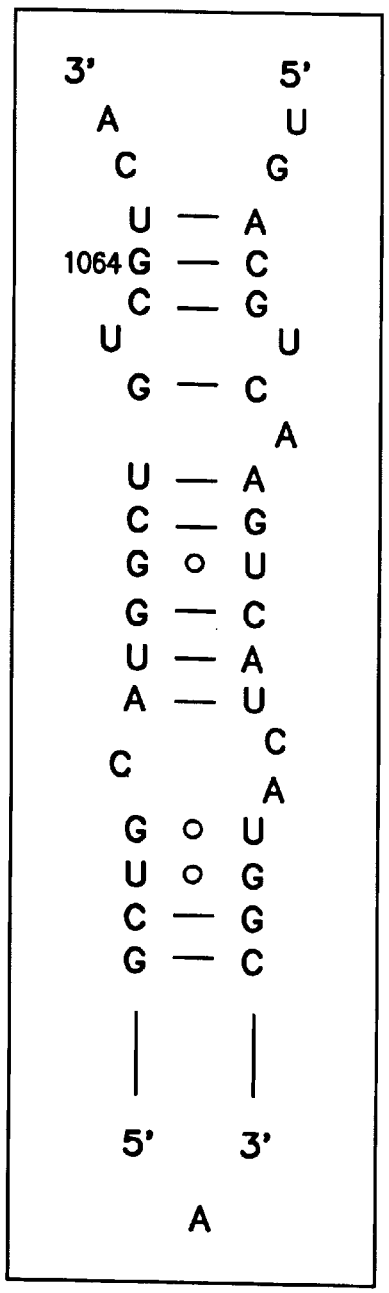
FIG. 4A is a representation of a region of the secondary structure of an RNA fragment encompassing helix 34 that confers resistance to spectinomycin.
Figure 4B:
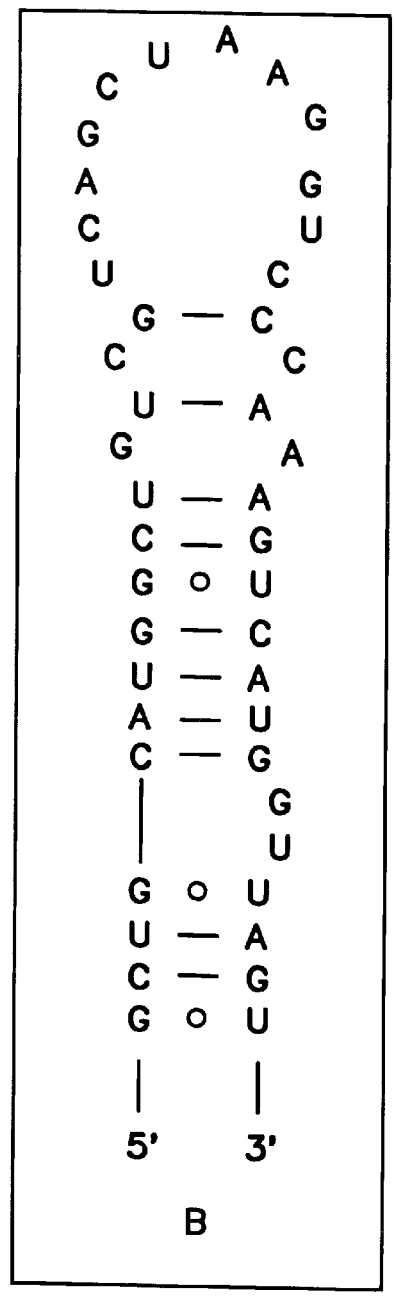
FIG. 4B is a representation of the predicted secondary structure of the 16/23S rRNA hybrid molecule: 16S rDNA AluI fragment (nucleotides 862–1068) and 23S rDNA AluI fragment (nucleotides 998–1099). Nucleotides common to helix 34 are in bold type.

Eight transformants harbored plasmids with the identical RNA fragments arising from the ligation between two rRNA fragments: a 16S rDNA AluI fragment (nucleotides 862–1068) was ligated immediately upstream of the 23S rDNA AluI fragment (nucleotides 998–1099) (FIG. 2). The 16S rDNA fragment contains the 5' half of helix 34 (including nucleotides 1050–1067). The 23S rDNA fragment encoded a nucleotide sequence identical to the primary sequence of the 3' half of helix 34 (nucleotides 1196–1202), thereby generating a hybrid helix 34 molecule (FIG. 4).

The simplest interpretation of this result is that the hybrid molecule is expressed at a sufficient level and is able to fold in a manner equivalent to that region of helix 34 involved in spectinomycin binding. Furthermore,it is apparent that primary sequences flanking helix 34, for example, nucleotides 1069–1190, are not essential to the drug binding. The 16/23S hybrid molecule shares common structure motifs with helix 34 including the G1064-C1192 base pair implicated in binding spectinomycin and is flanked by a potential non-Watson-Crick base pair (helix 34 U-U; 16/23S hybrid C-C) and bulged unpaired A residue also present in the wild type helix 34.

Chemical probing studies indicate that the upper stem region of helix 34 present in naked 16S rRNA becomes disrupted during assembly of the 30S subunit. Mutations that potentially stabilize this upper stem are deleterious and implicate the importance of this disruption for ribosome function. Spectinomycin is proposed to stabilize the upper stem, and thereby exert its inhibitory action. The lower stem of helix 34 also has the potential to undergo a conformational change without disruption of the overall base pairing arrangement (FIG. 2).

By contrast, the predicted lower helical stem in the 16/23S hybrid molecule is apparently stable. Transformants expressing the 16/23S RNA exhibit a higher level of spectinomycin resistance than those encoding the wild type helix 34 fragment molecule. Although this latter observation may reflect alternate stabilities of the two RNA fragment types, the drug binding site may be influenced by the nature and stability of the lower helix. The conformational flexibility of the lower stem may be important for protein synthesis.

Both molecules have the potential to form the lower helix (relative to the bulged A residue), whereas formation of the upper helix present in the wildtype helix 34 is not obvious for the hybrid molecule.

The precise nature of these transcripts in terms of their secondary structure is examined, as well as and whether they form a RNP complex necessary for spectinomycin binding. A number of proteins have been proposed to interact at or near helix 34. Spectinomycin-resistance mutations have been mapped to r-protein S5 [Bollen et al., Science, 165:85–86 (1969)] and crystallographic studies indicate an interaction between this protein and helix 34 [Ramakrishnan et al., Nature (London), 358:768–771 (1992)]. The identical protection patterns by r-protein S2 and S3 in helix 34 [Stem et al., Science, 224:783–790 (1989)] are not believed to be due to direct interactions but rather to conformational changes in the RNA and, are proposed to facilitate an interaction between helix 34 and S5, which stabilizes the new and functional RNA conformation. The hybrid molecule of Example 2 above lacks the sequences flanking helix 34 that show unique protection patterns in the presence of S2 and S3.

The functional activities of the translation termination factors RF1 and RF2 are influenced by point mutations within helix 34 [Prescott et al, Nucl. Acids Res., 7:1567–1571 (1992)] and their location according to immunoelectron microscopy studies is consistent with their being close to this helix [Moffat et al., Biochim., 73:1113–1120 (1991); Tate et al., Biochem. Int., 17:179–186 (1988)].

Spectinomycin binds to the naked RNA fragments rather than a RNP complex based on the following reasoning. While the rRNA fragments are constitutively expressed, expression of the r-proteins and the intact rRNAs is under strict control that is growth-rate regulated. Secondly, the 16S/23S hybrid fragment does not include flanking sequences characteristic of the wild-type domain to which the r-proteins have been mapped by footprinting methods (S2, S3, S5; Stern et al., cited above).

It is possible that a stable RNP complex or a transient one may exist, formed, e.g., by one or more of the translation factors. Spectinomycin has been proposed to affect translocation by inhibiting the binding of elongation factor G(EF-G) to the ribosome [Bilgin et al., EMBO J., 9:735–739 (1990)]. Mutations at position 1192 in 16S rRNA and in S5 decrease the inhibitory effect of spectinomycin on the EF-G cycle during peptide elongation. Footprinting studies with EF-G bound to the ribosome do not show any interaction between this factor and helix 34 [Moazed et al., Nature (London), 334:362–364 (1988)]. This is, however, in contrast with similar studies using the eukaryotic homologue, translation elongation factor 2 (EF-2 is equivalent to EF-G), bound to eukaryotic ribosomes that do show factor-dependent protection of nucleotides within the equivalent helix, 18S rRNA [Dumont-Miscopein et al., *FEBS Lett.*, 356:283–286 (1994)]. Together, these data provide support for an interplay between the small ribosomal subunit and an elongation factor (EF) that interacts principally on the large ribosomal subunit.

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A method for identifying an RNA fragment that mimics the structure of a binding site of a defined target RNA molecule, the method comprising the steps of:
   (a) providing a defined DNA fragment;
   (b) cloning said DNA fragment into a plasmid which under suitable conditions permits synthesis of said RNA fragment encoded by said DNA fragment,
   (c) transfecting said plasmid into a host cell which contains said target RNA molecule;
   (d) culturing an untransfected host cell in the presence of a compound, which compound binds the binding site of said target RNA molecule inside the host cell, resulting in inhibition or cessation of cell growth;
   (e) culturing said transfected host cells in the presence of said compound and determining cells transfected with the plasmid which permit the synthesis of an RNA fragment that mimics said target molecule, thereby conferring resistance to said compound to the transfected cells; and
   (f) isolating and characterizing the DNA fragment in the plasmid which encodes an RNA fragment thereby identifying an RNA fragment which mimics the structure of the binding site of said target molecule.

2. The method according to claim 1 wherein said defined target RNA molecule is a predetermined RNA sequence selected from the group consisting of RNA from a microorganism, an RNA expressed by a cell infected with a virus, a predetermined RNA sequence present in a mammalian cell, an RNA sequence encoded by a predetermined genomic sequence; and an RNA sequence encoded by a chemically synthesized DNA sequence.

3. The method according to claim 2 wherein said RNA is selected from the group consisting of ribosomal RNA, RNA encoded by a gene, messenger RNA, LTRs, transfer RNA, ribozyme RNA, catalytic RNA, splicesomal RNA, small nuclear RNA, and small nucleolar RNA.

4. The method according to claim 2 wherein said microorganism is selected from the group consisting of bacteria, yeast, fungi, protozoa, parasites and virus.

5. The method according to claim 1 wherein said defined DNA fragment is a DNA fragment of predetermined sequence produced by fragmenting DNA which encodes said target RNA molecule with a restriction enzyme.

6. The method according to claim 1 wherein said defined DNA fragment is a DNA fragment of predetermined sequence produced by chemical synthesis.

7. The method according to claim 1 wherein said host cell is of the same species as the cellular source from which the DNA encoding the RNA target molecule was derived.

8. The method according to claim 1 wherein said host cell is a cell from a different species from the cellular source from which said DNA encoding the RNA target molecule was derived.

9. The method according to claim 1 wherein said DNA was derived from a virally infected cell.

10. The method according to claim 9 wherein said cell is a mammalian cell.

11. A method for screening compounds and identifying a compound which binds a defined RNA fragment that mimics a binding site present on a target RNA molecule, said method comprising the steps of:
   (a) providing an untransfected host cell as a control;
   (b) providing a host cell transfected with a plasmid comprising a DNA sequence encoding said defined RNA fragment which mimics the binding site of said target RNA molecule;
   (c) exposing both host cells (a) and (b) to a library of compounds;
   (d) identifying a compound in the presence of which the growth of cells (a) is inhibited or destroyed; and in the presence of which, normal growth is observed for cells (b), said compound being thereby identified as binding to said defined RNA fragment.

12. A method for screening compounds and identifying a compound which retard cell growth or kill cells which contain a target RNA molecule comprising the steps of:
   exposing an RNA fragment that mimics a binding site present on said target RNA molecule to a library of compounds;
   identifying any compound which binds to said fragment; and
   exposing said compound to an untransfected host cell to detect inhibition or cessation of cell growth thereby identifying compounds which retard cell growth or kill cells which contain a target RNA molecule.

13. A method for identifying an RNA fragment that mimics the structure of a binding site of a defined target RNA molecule, the method comprising the steps of:
   (a) providing multiple random DNA fragments from DNA encoding said target molecule;
   (b) cloning each fragment into an identical plasmid resulting in a library of plasmids which under suitable conditions permits synthesis of the RNA fragments encoded by said DNA fragments, thereby generating a random RNA fragment library;
   (c) transfecting said plasmid library into a host cell which contains said target RNA molecule;
   (d) culturing said transfected host cells in the presence of a compound which binds said binding site of said target RNA molecule inside of said host cell, the binding resulting in inhibition or cessation of cell growth;
   (e) identifying host cells transfected with a plasmid that permits synthesis of an RNA fragment that mimics said target molecule, thereby conferring resistance to said compound to said host cell;
   (f) identifying host cells transfected with a plasmid that does not permit synthesis of a mimicking RNA fragment, which cells exhibit growth inhibition or cessation;
   (g) isolating plasmids from said resistant cells; and
   (h) identifying and characterizing from said plasmids of step (g) the DNA encoding the mimicking RNA fragment.

14. A method for screening compounds and identifying a compound which binds a random RNA fragment that mimics a binding site present on a target RNA molecule, said method comprising the steps of:
   (a) providing an untransfected host cell as a control;
   (b) providing a host cell transfected with plasmids, each plasmid comprising a random DNA sequence encoding a random RNA fragment which mimics the binding site of said target RNA molecule;
   (c) exposing both cells (a) and (b) to a library of compounds; and
   (d) identifying a compound in the presence of which the growth of cells (a) is inhibited or destroyed; and in the presence of which, normal cell growth is observed for cells (b), said compound being thereby identified as binding to a mimicking RNA fragment.

15. A method for identifying an RNA fragment that mimics the structure of a binding site of an undefined target RNA molecule and a compound that binds said RNA fragment, the method comprising the steps of:
   (a) providing random DNA fragments from a selected source;
   (b) cloning each fragment into an identical plasmid resulting in a library of plasmids which under suitable conditions permits synthesis of the RNA fragments encoded by said DNA fragments, thereby generating a random RNA fragment library;
   (c) transfecting said plasmid library into a host cell which contains RNA from said source;
   (d) culturing said transfected host cells in the presence of a library of compounds;
   (e) identifying host cells which exhibit growth inhibition or cessation of growth in the presence of a compound, which growth characteristics indicate that said compound has an effect on the host cell of inhibiting or ceasing cell growth;
   (f) identifying host cells which are resistant to said growth effects in the presence of the same compound, which indicates that an RNA fragment expressed by said transfected cell confers resistance to said compound on said host cell;
   (g) identifying said compound;
   (h) isolating plasmids from said resistant cells; and
   (i) identifying and characterizing from said plasmids of step (f) the DNA encoding an RNA fragment which mimics the binding site of said compound on said undefined target thereby identifying an RNA fragment that mimics the structure of a binding site of an undefined target RNA molecule and a compound that binds said RNA fragment.

16. The method according to claim 15, further comprising comparing the secondary structure of two or more RNA fragments identified in step (g) which confer resistance to the same compound and identifying a DNA fragment which encodes a common RNA structural motif in said two or more RNA fragments, thereby identifying a defined RNA fragment of the target molecule.

17. The method according to claim 16, further comprising screening a library of RNA sequences to determine the source of said defined RNA fragment and identifying said RNA target molecule thereby.

18. The method according to claim 15 wherein said undefined target RNA molecule is a random RNA sequence selected from the group consisting of RNA from a microorganism, an RNA expressed by a cell infected with a virus, and an RNA sequence present in a mammalian cell, an RNA sequence encoded by a random genomic sequence; an RNA sequence encoded by a library of chemically synthesized DNA sequence.

19. The method according to claim 15 wherein said random DNA fragment is a DNA fragment of unknown sequence.

20. A method for identifying an RNA fragment that mimics the structure of a binding site of a defined target RNA molecule, the method comprising the steps of:
   (a) providing multiple DNA fragments;
   (b) cloning each fragment into an identical plasmid resulting in a library of plasmids which under suitable conditions permits synthesis of the RNA fragments encoded by said DNA fragments, thereby generating a random RNA fragment library;
   (c) transfecting said plasmid library into a host cell which contains said target RNA molecule;
   (d) culturing said transfected host cells in the presence of a compound which binds said binding site of said target RNA molecule inside of said host cell, the binding resulting in inhibition or cessation of cell growth;
   (e) identifying host cells transfected with a plasmid that permits synthesis of an RNA fragment that mimics said target molecule, thereby conferring resistance to said compound to said host cell;
   (f) identifying host cells transfected with a plasmid that does not permit synthesis of a mimicking RNA fragment, which cells exhibit growth inhibition or cessation;
   (g) isolating plasmids from said resistant cells; and
   (h) identifying and characterizing from said plasmids of step (g) the DNA encoding the mimicking RNA fragment.

21. The method of claim 15 further comprising the steps of (a) isolating a plasmid from the host cells which contain a plasmid which contains a random DNA encoding a mimicking RNA fragment; and (b) identifying and characterizing said random DNA encoding said mimicking RNA fragment, thereby producing a defined DNA fragment encoding a defined RNA fragment for further screening.

* * * * *